United States Patent
Roustan et al.

(10) Patent No.: US 6,225,502 B1
(45) Date of Patent: May 1, 2001

(54) USE OF AN ANILINE DEPLETED IN ELECTRON TO RELEASE HYDROCHLORIC ACID PRESENT IN A REACTION MIXTURE AND METHOD FOR DISPLACING, AT LEAST PARTIALLY, AN ANILINE FROM ITS CHLORHYDRATE

(75) Inventors: Alain Roustan, St-Genis Laval; Philippe-Jean Tirel, Communay, both of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/445,717
(22) PCT Filed: Jun. 24, 1998
(86) PCT No.: PCT/FR98/01334
§ 371 Date: Dec. 9, 1999
§ 102(e) Date: Dec. 9, 1999
(87) PCT Pub. No.: WO98/58900
PCT Pub. Date: Dec. 30, 1998

(30) Foreign Application Priority Data

Jun. 24, 1997 (FR) .................................................. 97 07872

(51) Int. Cl.$^7$ ..................................................... C07C 209/00
(52) U.S. Cl. .................................................................. 564/437
(58) Field of Search ............................................... 564/437

(56) References Cited

PUBLICATIONS

Albert E. Beguin et al.; Journal of the American Chemical Society XP002057611, DC, US; 2–1939.
Panos Grammaticakis: Bulletin de la Societe Chimique de France XP00257612, Paris, FR; 2–1967.
G.C. Finger et al.: Journal of Medicinal Chemistry, XP002057613, Washington, US; 7–1964.
Saul Patai: Interscience, London—New York—Sydney XP002057614; 1968 month unavailable.

*Primary Examiner*—Samuel Barts
(74) *Attorney, Agent, or Firm*—Jean-Louis Seugnet

(57) ABSTRACT

The invention concerns a method for displacing, at least partially, an aniline from its chlorhydrate, characterized in that said aniline is selected among anilines whereof the conjugate acid has a pKa not more than 6 and in that it consists in a step wherein it is subjected at a temperature not less than 50° C., advantageously about 70° C. to a reaction medium containing said chlorhydrate at least partially dissolved in a weakly polar solvent. The invention is applicable to organic synthesis.

19 Claims, No Drawings

USE OF AN ANILINE DEPLETED IN ELECTRON TO RELEASE HYDROCHLORIC ACID PRESENT IN A REACTION MIXTURE AND METHOD FOR DISPLACING, AT LEAST PARTIALLY, AN ANILINE FROM ITS CHLORHYDRATE

This application is an application under 35 U.S.C. Section 371 of International application No. PCT/FR98/01334, filed on Jun. 24, 1998.

The subject-matter of the present invention is the use of electron-depleted aniline for releasing hydrochloric acid present in a reaction mixture and [lacuna] process for displacing, at least partially, an aniline from its hydrochloride. It relates more particularly to a process for displacing, at least partially, an aniline from its hydrochloride.

There are numerous synthetic reactions in chemistry which give off hydrochloric acid. Among these reactions, some release hydrochloric acid without specific measures having to be taken to achieve this.

Other reactions involve amines or require the presence of bases and thus result in the formation of salts of hydrochloric acid and in particular of hydrochloride. It is reactions of this type which are targeted by the present invention.

The treatment of salts of hydrochloric acid is extremely expensive and results in discharges which are sometimes supposed to be polluting and are always subject to regulatory control.

Mention may be made, among the reactions targeted, of alkylation reactions [in the present description, ALK-yl is taken in its etymological sense of hydrocarbon-comprising residue of an ALK-ohol, with the alcohol (or ohol) functional group being ignored] on chalcogen atoms or on atoms from Group V-B (Periodic Classification of the Elements as published in the Supplement of the Société Chimique de France, No. 1, January 1966).

Mention may in particular be made of the reaction of alkyl chloride with carboxyl functional groups and with phenol functional groups, as well as with amino functional groups, reactions which are supposed only to take place in the presence of the basic form of the functional groups to be alkylated.

It is also appropriate to mention the reactions of acid chloride, and in particular of acyl chloride, with nucleophilic substrates and in particular the substrates carrying the functional groups and/or atoms mentioned above.

The decomposition of aniline hydrochlorides and more generally amine hydrochlorides has been described previously, but these techniques employ very high temperatures, generally far above 200° C., and these techniques require the use of crystalline or solid hydrochloride.

Furthermore, such techniques are expensive and are not applicable to molecules which are unstable or volatile under the conditions of the decomposition of the hydrochloride.

This is why one of the aims of the present invention is to provide a technique which makes it possible to release hydrochloric acid present in an organic medium in the form of the hydrochloride of certain anilines.

Another aim of the present invention is to provide a process of the above type which makes it possible to obtain dry hydrochloric acid.

Another aim of the present invention is to provide a process which makes it possible to release an aniline from its hydrochloride at the same time as a reaction which releases hydrochloric acid is carried out simultaneously.

Another aim of the present invention is to provide a process which makes possible the alkylation or the acylation of specific anilines present, at least partially, in the form of their hydrochlorides in the reaction mixture.

These aims, and others which will become apparent subsequently, are achieved by means of a process for displacing, at least partially, an aniline from its hydrochloride, the said aniline in the process being chosen from anilines with a conjugate acid exhibiting a pKa at most equal to 6 and the process comprising a stage in which a reaction mixture comprising the said hydrochloride, at least partially dissolved in a lipophilic medium, is subjected to a temperature at least equal to approximately 50° C. (in the present description, the term "approximately" is employed in order to emphasize the fact that, when the figure or figures the furthest to the right of a number are zeros, these zeros are positional zeros and not significant figures, unless, of course, otherwise specified), advantageously to approximately 70° C.

The reaction is carried out at a temperature at most equal to approximately 200° C., advantageously at most to 200° C. (three significant figures), preferably to approximately 180° C.

The lipophilic medium can be in particular a weakly polar solvent or one of the reactant in excess, in particular the said aniline, alone or dissolved in a weakly polar solvent.

According to the present invention, it is preferable for the said aniline to exhibit a pKa at most equal to 5, advantageously 4, preferably to 3.

The solubility in weakly polar media also plays a significant role in the implementation of the present invention. It is therefore desirable for the solubility of the hydrochloride of the said aniline in benzene to be at least sparingly soluble (δ or d), advantageously at least soluble(s), preferably very soluble (v). The symbols are those used in the reference work *Handbook of Chemistry and Physics*.

Furthermore, it is desirable for the lipophilic medium to be weakly miscible with water and to be sufficiently hydrophobic not to be miscible with water in any proportion. It is thus preferable for water to be able to dissolve only at most 10% of the solvent or that which is acting as solvent; this limit is advantageously at most 5%, preferably at most 2%, by mass, advantageously even in the presence of the substrate as third solvent.

It is likewise preferable for the solvent to be able to dissolve only at most 10% of water, advantageously at most 5%, preferably at most 2%, by mass, advantageously even in the presence of the substrate as third solvent.

The term "weakly polar solvent" should be understood as meaning a solvent with a dielectric constant [which changes comparatively little with temperature but which is advantageously measured at about 20° C.; reference may be made, for dielectric constant values, to the fourth edition of the work published by John Wiley and Sons, "Techniques of Chemistry; Organic Solvents, Physical Properties and Methods of Purification", by John A. Riddick, William B. Bunger and Théodore K. Sakano] at most equal to approximately 10 (relative dielectric constant $\in$). This value of $\in$ is valid for the main constituent of the solvent but it is preferable for the whole solvent to correspond to this constraint.

The maximum value of $\in$ is advantageously at most equal to 10 (two significant figures), preferably to 5 (value of chlorobenzene).

According to the present invention, it is preferable for the main constituent of the solvent to be weakly basic, that is to say for its donor index or donor number to be at most equal to approximately 20, preferably at most equal to 20 (two significant figures). The lower limit does not have a critical nature.

Reference may be made, for the definition of the donor number, to the work by Christian Reinhardt, *Solvents and Solvents Effects in Organic Chemistry*, p. 19 (1988), which work gives, as definition, the negative of the enthalpy (−ΔH, expressed in kilocalories/mol) of the interaction between the solvent and antimony pentachloride in a dilute dichloroethane solution.

However, when mixtures of different compounds are used as solvents, it may be advantageous for one of them, in a minor proportion, to exhibit a degree of basicity.

The solvents can be mixtures, including petroleum fractions. Naturally, under the operating conditions, the solvents must be inert with regard to the substrates and reactants used.

Preferred families of solvents are chosen from the group consisting of hydrocarbons, aromatic derivatives, ethers, esters and halogenated solvents.

Mention may be made, as paradigms of these families, as halogenated aliphatic derivatives, of dichloromethane, 1,2-dichloroethane or 1,1,1-trichloroethane, as aromatic derivatives, of toluene, and as halogenated aromatic derivatives, of chlorobenzene, as esters, of ethyl acetate and isopropyl acetate, as ethers, of tert-butyl methyl ether, as well as anisole and heavy alcohols, that is to say corresponding to the restrictions of immiscibility as specified above.

For reasons of industrial economy, it is preferable to be able to distil the solvent at atmospheric pressure or under low or ultrahigh vacuum.

It is preferable for the said weakly polar solvent to be chosen from solvents with an aromatic nature, that is to say from solvents which exhibit at least one aromatic nucleus. This aromatic nucleus can either be present in a minor or major constituent of the solvent or, when the solvent is composed of a single compound, can be present in this compound.

The solvent must be chosen so that its melting point is lower than the temperature at which the reaction has to be carried out. Thus, it is desirable to use weakly polar solvents from aromatic solvents which involve a melting temperature of the reaction mixture of at most 70° C., advantageously of at most 50° C.

The weakly polar solvent is generally a solvent chosen from aliphatic and/or aromatic hydrocarbons, halogenated aromatic derivatives, esters, phenol ethers and their mixtures.

In addition, it is advantageous to choose the solvent so that its starting boiling temperature is below the boiling temperature (or sublimation temperature) of the amine and, if appropriate, of the other reactants employed in the process.

According to the present invention, it is desirable for the aniline which is the subject-matter of the present invention to exhibit an electron-depleted nucleus. This depletion can be obtained in particular by grafting, to the nucleus, electron-withdrawing groups or electron-withdrawing functional groups which advantageously withdraw via an inductive effect.

Thus, a nucleus as depleted as that of a dichlorobenzene (corresponding to a dichlorophenyl radical) already gives good results.

Of course, the depletion can be greater. Mention may be made, among the electron-withdrawing functional groups of particular advantage, of halogens, advantageously light halogens, chlorine and fluorine; groups carrying two halogens on the carbon attached to the nucleus and more particularly trihalomethyl groups and more especially trifluoromethyl groups and pseudohalogen groups (see below).

Electron-withdrawing groups which withdraw via a mesomeric effect can be of advantage in some cases and in particular groups carrying carbonyl functional groups, such as ester groups.

These electron-withdrawing atoms are advantageously as weakly polar as possible, that is to say they must not interfere with the solubility of the hydrochloride of the amine in the weakly polar solvents.

It is desirable for the aromatic nucleus carrying the aniline functional group to be made as lipophilic as possible. To do this, the nucleus can carry very lipophilic groups, among which may be mentioned highly fluorinated groups and in particular perfluorinated groups, silylated groups and chains of at least three carbon atoms.

In the present description, a radical is regarded as a pseudohalogen [in general, this radical has a light chalcogen (sulfur or, preferably, oxygen) by which it is connected to the remainder of the molecule] which, on leaving, constitutes an anion for which the associated acid exhibits an acidity, measured by the Hammett constant, at least equal to that of acetic acid. Mention may be made, among typical pseudohalogens, of acyloxyl radicals corresponding to acids perhalogenated at the alpha position of the acyloxyl functional group, such as trifluoroacetyloxyl ($CF_3$—CO—O—), and especially sulfonyloxyl radicals and especially those for which the carbon carrying the sulfur is perfluorinated, the paradigm of which is trifluoromethylsulfonyloxyl.

According to the present invention, alkoxycarbonyloxyls, which exhibit an acceptable lipophilicity and an acceptable electron-withdrawing effect, while being cheaper, are also targeted.

Among pseudohalogens, the best electron-withdrawers are those which, on leaving, exhibit an acidity at least equal to that of sulfonic acids, such as tosylic acid (paradigm of arylsulfonic acids) or mesylic acid (paradigm of alkylsulfonic acids).

Mention should also be made of those which correspond to perfluoroalkylsulfonic acids which exhibit both a good electron-withdrawing effect and a good increase in the lipophilicity.

Advantageous results were obtained in the case where the said aniline exhibited, on the same nucleus, a phenol ester functional group.

Thus, according to the present invention, it is desirable for the said aniline to exhibit, [lacuna] the same nucleus, a phenol ester functional group and at least one other electron-withdrawing functional group which can be chosen from chlorine and/or fluorine atoms. Although it is slower, the reaction can be carried out with an aniline exhibiting, on the same nucleus, a phenol ether functional group and at least two other electron-withdrawing functional groups which can be chosen from chlorine and/or fluorine atoms.

The present invention is particularly advantageous when it is carried out in combination with a reaction which gives off hydrochloric acid. In this case, the aniline provides the base necessary to bring to a successful conclusion or to facilitate the reaction which gives off hydrochloric acid and, on the other hand, facilitates the evolution of gaseous hydrochloric acid.

This reaction can be in particular an alkylation reaction on the aniline itself or, preferably, an acylation reaction on the aniline itself.

This acylation reaction is advantageously an alkoxycarbonylation reaction.

However, the aniline can simply act as catalyst, insofar as it is found intact at the end of the reaction; it can, in that case, facilitate the formation of nucleophilic forms in reactants, absorb hydrochloric acid thus given off and then release it in the gaseous form.

To facilitate the reaction, it is advisable to replace the gas phase in contact with the liquid phase of the reaction mixture. To do this, gaseous flushing can be used, which flushing can be obtained either by sparging with an inert gas or by evaporating a liquid or a solid within a reaction mixture.

This liquid or this solid can be a constituent of the solvent and the flushing can be achieved by carrying out the reaction at reflux of the constituent of a solvent.

It is preferable for the constituent components of the solvent and particularly that with the lowest boiling point, which will regulate the reaction temperature and will facilitate the removal of hydrochloric acid, not to form a strong combination with the hydrochloric acid. In particular, it is preferable for there to be no formation of azeotrope or of definite compound with hydrochloric acid, at any event in the gas phase.

Use may also be made of another parameter in carrying out the reaction, which is to vary the pressure at which the reaction is carried out, so as to bring the starting boiling temperature to the desired reaction temperature.

When it is desired to use amines as catalyst, it is advisable for the aniline functional group to be difficult to acylate or alkylate. Thus, anilines which are doubly substituted on the nitrogen by alkyl radicals are recommended.

Generally, the total carbon number of the said anilines is advantageously between 6 and 20.

The best results obtained were achieved with anilines with a nucleus carrying a perfluoroalkyl group.

In the present description, the term "perfluoroalkyl" (Rf) is understood to mean radicals perfluorinated on the carbon carrying the bond with the aryl (advantageously phenyl), the which perfluoroalkyl advantageously corresponds to the formula:

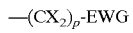

—(CX$_2$)$_p$-EWG where the X groups, which are alike or different, represent a fluorine or a radical of formula C$_n$F$_{2n+1}$, where n is an integer at most equal to 5, preferably to 2;

where p represents an integer at most equal to 2;

where EWG represents an electron-withdrawing group (including a chlorine atom or a —CF$_2$— linkage carrying an alkyl or aryl radical), the possible functional groups of which are inert under the reaction conditions, advantageously a fluorine atom or a perfluorinated residue of formula C$_n$F$_{2n+1}$, with n an integer at most equal to 8, advantageously to 5. The total carbon number of Rf is advantageously between 1 and 15, preferably between 1 and 10.

Other particularly advantageous results were obtained starting from anilines where the nucleus carried two halogens (the two halogens advantageously being two chlorines, two fluorines or a chlorine and a fluorine) and a phenol functional group blocked by an acyl, including in particular by an alkoxycarbonyloxyl. The acyl group advantageously comprises at least three, preferably at least four, carbons, to ensure good lipophilicity. However, it is desirable for the acyl group not to comprise more than 15 carbon atoms, referably not more than 10 carbon atoms.

The following nonlimiting examples illustrate the invention:

EXAMPLE 1

Action of ethyl chloroformate on meta-(trifluoromethyl) aniline

A toluene solution of trifluoromethylaniline is charged in a reaction. The mixture is degassed, placed under a nitrogen blanket and brought to 85° C. Once at a temperature of 85° C., a stoichiometric amount of ethyl chloroformate is run in slowly over a period of three hours. After the ethyl chloroformate has been run in, the temperature is maintained for two hours, the temperature is then brought to reflux of the toluene and reflux is maintained for two hours until the end of the reaction. After these two hours, the acylation reaction, as well as the reaction for removal of the hydrochloric acid given off, are complete. The yields are substantially quantitative with respect to the amine introduced.

Similar results are obtained with dihalogenated aminophenols, the alcohol functional group of which is blocked by a lipophilic pseudohalogen of at most 7 carbon atoms (carbonate and sulfonate).

EXAMPLE 2

Partial release of meta-TFMA from its hydrochloride

A xylene solution of trifluoromethylaniline (TFMA) is charged to a reactor. The mixture is degassed, placed under a nitrogen blanket and brought to reflux of the xylene, and reflux is maintained for three hours. After these three hours, the hydrochloric acid given off is of the order of 15% of the hydrochloride introduced and is uninterrupted.

What is claimed is:

1. A process for displacing, at least partially, an aniline from its hydrochloride, said aniline having a conjugate acid exhibiting a pKa at most equal to 6, an electron-depleted nucleus and, grafted to the nucleus, an electron-withdrawing group via an inductive effect, an electron-withdrawing functional group via an inductive effect, or a carbonyl carrying group, said process comprising the steps of:

a) heating a reaction mixture comprising said hydrochloride, at least partially dissolved in a lipophilic medium, to a temperature at least equal to about 50° C. in order to give off hydrochloric acid and release it in the gazeous form.

2. A process according to claim 1, wherein said temperature is at least equal to about 70° C.

3. A process according to claim 1, wherein the lipophilic medium is a weakly polar solvent.

4. A process according to claim 3, wherein said weakly polar solvent is an aromatic solvent.

5. A process according to claim 1, wherein the hydrochloride of said aniline is at least sparingly soluble in benzene.

6. A process according to claim 4, wherein said weakly polar solvent has a melting temperature lower than 70° C.

7. A process according to claim 4, wherein said weakly polar solvent is an aromatic hydrocarbon, a halogenated aromatic derivative, an ester, a phenol ether or their mixtures.

8. A process according to claim 3, wherein the starting boiling temperature of the solvent is below the boiling temperature or sublimation temperature of the amine.

9. A process according to claim 1, wherein said said carbonyl-carrying group is a phenol ester functional group.

10. A process according to claim 9, wherein said aniline exhibits, on the electron-depleted nucleus, the phenol ester functional group and another electron-withdrawing functional group.

11. A process according to claim 1, further comprising the step of:

b) carrying out another reaction on said aniline, in combination with said displacement reaction, which facilitates the evolution of hydrochloric acid of step a).

12. A process according to claim 11, wherein, in step b), said another reaction is an alkylation or an acylation.

13. A process according to claim 11, wherein in step b), said another reaction is an alkoxycarbonylation.

14. A process according to claim 1, wherein there is a gas phase in contact with the reaction mixture which is in liquid phase and said gas phase is replaced by using gaseous flushing.

15. A process according to claim 14, wherein the gaseous flushing is obtained either by sparging with an inert gas or by evaporating a liquid or a solid within the reaction mixture.

16. A process according to claim 14, wherein the gas phase is replaced by bringing the reaction mixture to reflux of one of its constituents, said constituent not forming an azeotrope with hydrochloric acid.

17. A process according to claim 1, wherein the reaction is carried out under a pressure other than atmospheric pressure, so as to bring the reaction mixture to the desired reaction temperature.

18. A process according to claim 1, wherein said aniline is meta-(trifluoromethyl)aniline.

19. A process according to claim 1, wherein in step a) said temperature is at most equal to about 200° C.

* * * * *